(12) United States Patent
Liao et al.

(10) Patent No.: US 9,533,130 B2
(45) Date of Patent: Jan. 3, 2017

(54) SYRINGE

(71) Applicant: Taiwan Biomaterial Co., Ltd., Douliou, Yunlin County (TW)

(72) Inventors: Chun-Jen Liao, Taipei (TW); Wen-Hsi Wang, Taipei (TW); Yu-Ming Wang, Tainan (TW); Yu-Chung Chang, New Taipei (TW); Hsin-Yu Wu, Erlun Township, Yunlin County (TW); Ping-Chuan Chen, Hsinchu (TW)

(73) Assignee: TAIWAN BIOMATERIAL CO., LTD., Douliou, Yunlin County (TW)

( * ) Notice: Subject to any disclaimer, the term of this patent is extended or adjusted under 35 U.S.C. 154(b) by 60 days.

(21) Appl. No.: 14/504,835

(22) Filed: Oct. 2, 2014

(65) Prior Publication Data
US 2015/0273194 A1 Oct. 1, 2015

(30) Foreign Application Priority Data

Mar. 27, 2014 (TW) .............................. 103111365 A

(51) Int. Cl.
*A61M 35/00* (2006.01)
*A61M 5/24* (2006.01)
(Continued)

(52) U.S. Cl.
CPC ...... *A61M 35/003* (2013.01); *A61B 17/00491* (2013.01); *A61J 1/2089* (2013.01); *A61J 1/2096* (2013.01); *A61M 5/2466* (2013.01); *A61M 5/31511* (2013.01); *A61B 2017/00548* (2013.01); *A61J 1/201* (2015.05); *A61J 1/2051* (2015.05);
(Continued)

(58) Field of Classification Search
CPC ................... A61B 17/00491; A61M 39/0606; A61M 5/145; A61M 5/31511; A61M 39/045; A61M 3/0233; A61M 5/31596; A61M 5/284; A61M 5/2448; A61M 5/2053; A61M 5/2429; A61M 2005/2407; A61M 5/2455; A61M 5/2466; A61M 5/285; A61M 5/288; A61M 2005/247; A61M 5/155; A61M 5/19; A61J 1/2003; A61J 1/2006; A61J 1/201
See application file for complete search history.

(56) References Cited

U.S. PATENT DOCUMENTS 3,977,401 A * 8/1976 Pike ........................ A61M 5/24
                                                         604/144
5,067,948 A * 11/1991 Haber et al. ................... 604/213
(Continued)

FOREIGN PATENT DOCUMENTS

WO          WO 0100261 A1 *  1/2001

*Primary Examiner* — Imani Hayman
*Assistant Examiner* — Hamza Darb
(74) *Attorney, Agent, or Firm* — Birch, Stewart, Kolasch & Birch, LLP

(57) ABSTRACT

A syringe includes a sleeve and a pressure vessel with high pressure fluid therein. The sleeve further comprises a sleeve piston. As the high pressure vessel contacts the sleeve piston, and a bump on the sleeve piston destroys the airtight status of the high pressure vessel. While the seal of the high pressure vessel is removed, the compressed fluid flows into the sleeve through the opening of the high pressure vessel and the hole of the sleeve piston. When the closed end of the sleeve moves closer to the closed end of the sleeve piston, the fluid in the sleeve is pressed and flows out of the sleeve through the sleeve hole of the sleeve.

14 Claims, 8 Drawing Sheets

(51) Int. Cl.
*A61J 1/20* (2006.01)
*A61M 5/315* (2006.01)
*A61B 17/00* (2006.01)
*A61M 5/28* (2006.01)

(52) U.S. Cl.
CPC .............. *A61J 1/2065* (2015.05); *A61M 5/288* (2013.01); *A61M 2005/2474* (2013.01); *A61M 2005/2488* (2013.01)

(56) References Cited

U.S. PATENT DOCUMENTS

| | | | |
|---|---|---|---|
| 6,096,002 A * | 8/2000 | Landau | ................... A61M 5/30 604/143 |
| 8,308,681 B2 | 11/2012 | Slocum et al. | |
| 2008/0138376 A1* | 6/2008 | Harman et al. | ............... 424/423 |
| 2012/0029471 A1* | 2/2012 | Lee et al. | ...................... 604/518 |

* cited by examiner

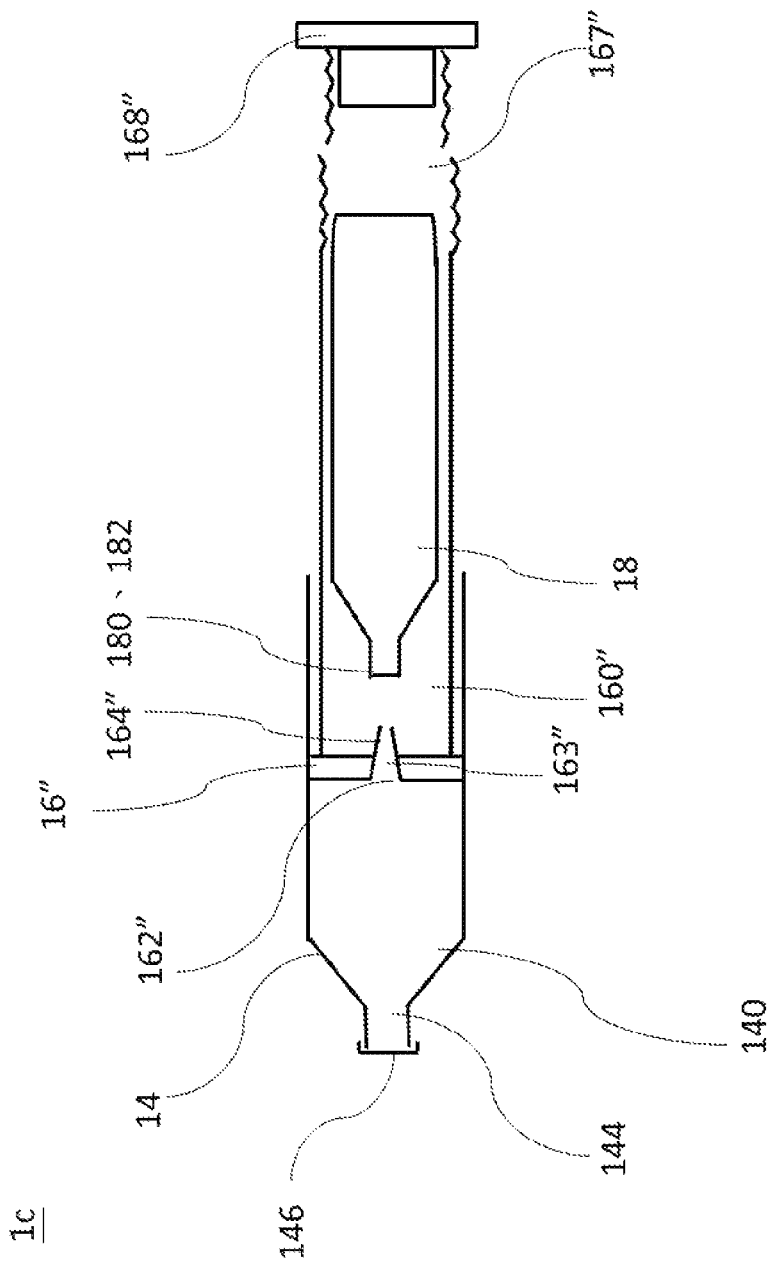

SYRINGE

FIELD OF THE INVENTION

The present invention relates to a syringe, and in particular to a syringe that is provided for ejecting a high pressure fluid.

BACKGROUND OF THE INVENTION

The most common form of the biological dressing material, such as collagen, is sponge. The lightweight and porous structure of sponge makes it suitable for tissue regeneration. However, this sponge has to be trimmed into an appropriate size before application since the shape and size of the sponge is preformed. Moreover, the surgeon has to soak the sponge before applying on surface of the defect site, which make it even more inconvenient and increases the uncertainty for the clinical application.

In contrast to dressing in sponge form, a foamy biomaterial is under development. It is a mixture of high-pressure gas and viscous gel. The above-mentioned mixture is stored at high pressure in container. Bubbles will be trapped inside the gel matrix to form a foamy material when the mixture is released from high pressure to ambient pressure. The porous, lightweight and fluidic nature of foamy material makes it convenient and suitable to fill the gap between tissues. Hence, foamy biomaterial has be stored in a container at high pressure in advance, and then release from high pressure to create a porous structure right before it is applied on the surface of the tissue.

For the use of the foamy material, the compressed mixture is directly decompressed and released by syringe into the desired covering surface, such as shaving foam, hairdressing foam or cleaning foam. Alternatively, the compressed mixture is decompressed and released in a temporary container, and the foamy material is spread to the desired position by tools or digging with one's hand. However, the tissue might be damaged if the foamy material applied directly on the surface of the tissue because of the high pressure. On the hand, the time of foamy material exposed to the environment will increase if using tool or hand to apply the material. Thus, the present invention provides a new apparatus for applying the foamy material.

SUMMARY OF THE INVENTION

The present invention is to provide a syringe with a high pressure container. The mixture sealed inside the container is released into a chamber within the syringe to produce a foamy material. The foamy material is then extruded by the syringe, and spread on the surface of the application site. The design of the syringe is not only convenient for user but also can reduce the uncertainty and lower the risk of the high pressure in medical application.

According to above objective, the present invention provides a syringe which includes a first sleeve, a sleeve piston and a pressure vessel. The first sleeve has an opening end and an engaged end which is opposite to the opening end. A sleeve opening is disposed at the opening end of the first sleeve. One end of a sleeve piston has a protrusion and a through-hole is communicated with two ends of the sleeve piston. The sleeve piston is disposed and being movable in the first sleeve. The other end of the sleeve piston without protrusion is toward the opening end of the first sleeve and a pitch is disposed between the other end of the sleeve piston without protrusion and the opening end of the first sleeve. The pressure vessel has a vessel opening which is sealed with a vessel lid and the vessel opening is opposite to the protrusion, in which the pressure vessel contains the fluid therein and the fluid is flowed into the first sleeve through the vessel opening and the through-hole.

With the syringe of the present invention, while the airtight status of the pressure vessel is destroyed, the fluid stored in the high pressure vessel is injected into the accommodating space of the first sleeve and then user presses to generate the relative movement between the first sleeve and the sleeve piston to inject the fluid out from the accommodating space of the first sleeve.

With the syringe of the present invention, the fluid stored in high pressure vessel is first decompressed and released into the chamber of the syringe under the normal pressure condition, and the fluid is then injected through the chamber of the syringe to spread on the required region to increase the convenience of use for the fluid is stored in high pressure vessel.

BRIEF DESCRIPTION OF THE DRAWINGS

The present invention will be apparent to those skilled in the art by reading the following description of a preferred embodiment thereof with reference to the drawings, in which:

FIG. 6 is a schematic section view of a syringe in a fourth embodiment in accordance with the present invention.

DETAILED DESCRIPTION OF THE PREFERRED EMBODIMENT

The object of present invention is to provide a syringe. Present subject matter is the unique structure of the syringe, and therefore, as to what substances that the syringe applying for, or the effects of substances that applying with the present syringe, are not the specific aim of present invention. In the following detailed description of the preferred embodiments, the reference is made to the accompanying drawings which form a part hereof, and as shown by way of illustration specific embodiments in which the invention may be practiced.

Figure 1A:
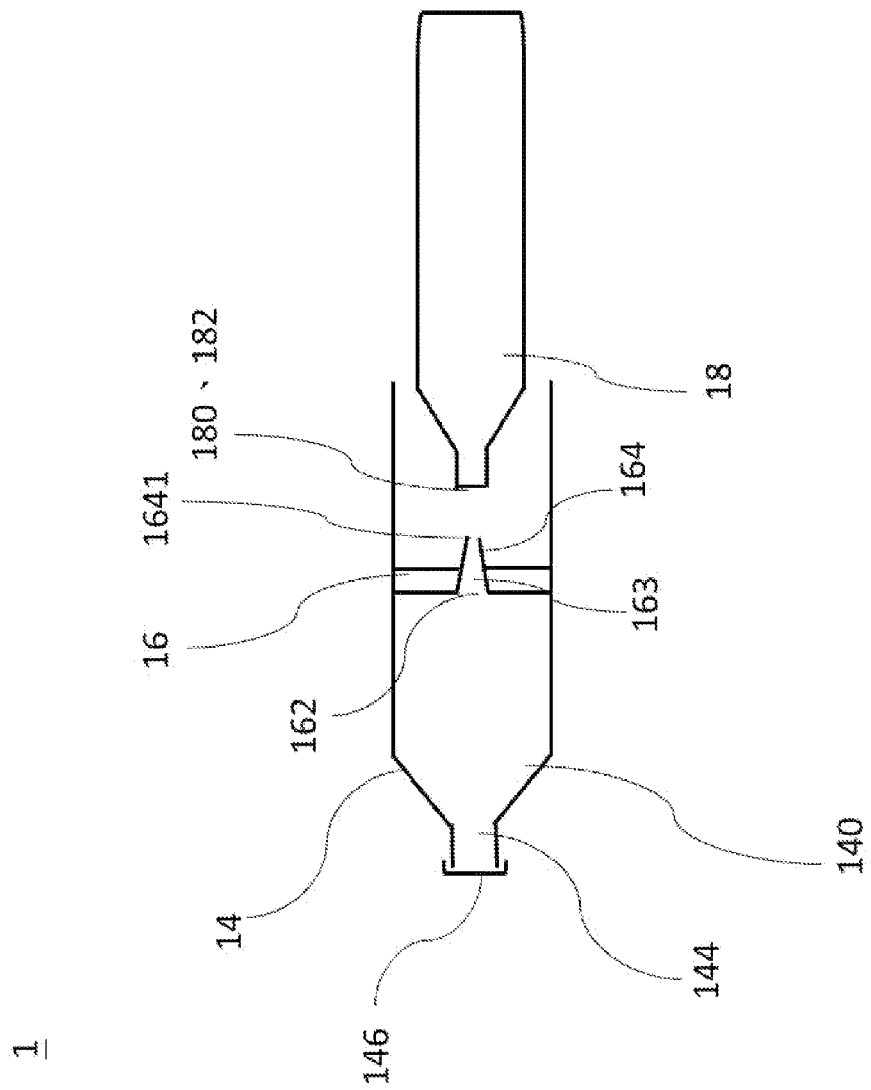
FIG. 1A is a schematic section view of a syringe of the first embodiment in accordance with the present invention.

Please refer to FIG. 1A. FIG. 1A shows a section view of a syringe 1 of the first embodiment of the present invention. As shown in FIG. 1A, the first sleeve 14 includes an opening end and an engaged end which is opposite to the opening end, and in the middle of the opening end and the engaged end are constructed to form a wall surface, in which the engaged end of the first sleeve 14 is an opening end. The sleeve piston 16 includes a through-hole 163. One end of the through-hole 163 is a piston front opening 162 and a protrusion 164 is formed around another end. The front end of the protrusion 164 is formed as an opening 1641. Two ends of the sleeve piston 16 is communicated with each other by the opening 1641 at the front end of the protrusion 164 and the through-hole 163, in which inside of the first sleeve 14 is an first accommodating space 140, the opening end of the first sleeve 14 includes a first sleeve opening 144 to communicate the first accommodating space 140 with outside of the sleeve 14. The first sleeve opening 144 is further sealed with a cover 146 thereon. When the sleeve piston 16 is disposed in the first sleeve 14, the piston front opening 162 of the sleeve piston 16 is disposed toward the engaged end of the first sleeve 14 and is accommodated into the first accommodating space 140 and a pitch is disposed between the sleeve piston 16 and the opening end of the first sleeve 14. One end of a pressure vessel 18 includes a vessel opening 180 so as to communicate with the outside of the pressure vessel 18. The vessel opening 180 includes a vessel lid 182 to seal the vessel opening 180. When the vessel lid 182 on the opening of the pressure vessel 18 is in an airtight status, the pressure vessel 18 can contain the fluid with a pressure that is larger than the environment pressure, for example, the pressure in the pressure vessel 18 is about 2 atm. In one embodiment, the fluid is a mixture by mixing high-pressure gas and colloidal and the mixture in the pressure vessel 18 is in a pressure range of 1 atm to 150 atm.

The pressure vessel 18 utilizes the vessel opening 180 toward to the accommodating space 140 to dispose into the first sleeve 14. When the sleeve piston 16 is contacted to the pressure vessel 18, the through-hole 163 is opposite and contacted to the vessel opening 180 to let the protrusion 164 to pierce through the vessel lid 182 so as to the through-hole 163 is communicated with inside of the pressure vessel 18 to destroy the airtight status of the pressure vessel 18. As previously mentioned, the storage pressure is larger than the environment pressure when the fluid is in the pressure vessel 18. Thus, when the vessel lid 182 is pierced and the through-hole 18 is communicated with inside of the pressure vessel 18, the fluid in the pressure vessel 18 will flow into the first accommodating space 140 of the first sleeve 14 through the piston front opening 162, in which the pressure in the first accommodating space 140 of the first sleeve 14 is smaller than that of in the pressure vessel 18. Thereafter, the vessel lid 146 is removed and the pressure vessel 18 presses the sleeve piston 16 toward inside of the first sleeve 14 such that the pitch is disposed between the sleeve piston 16 and the opening end of the first sleeve 14 is gradually to be shrunk, and the fluid in the first accommodating space 140 of the first sleeve 14 is compressed by the sleeve piston 16 to flow out from the first sleeve opening 144.

Figure 1B:
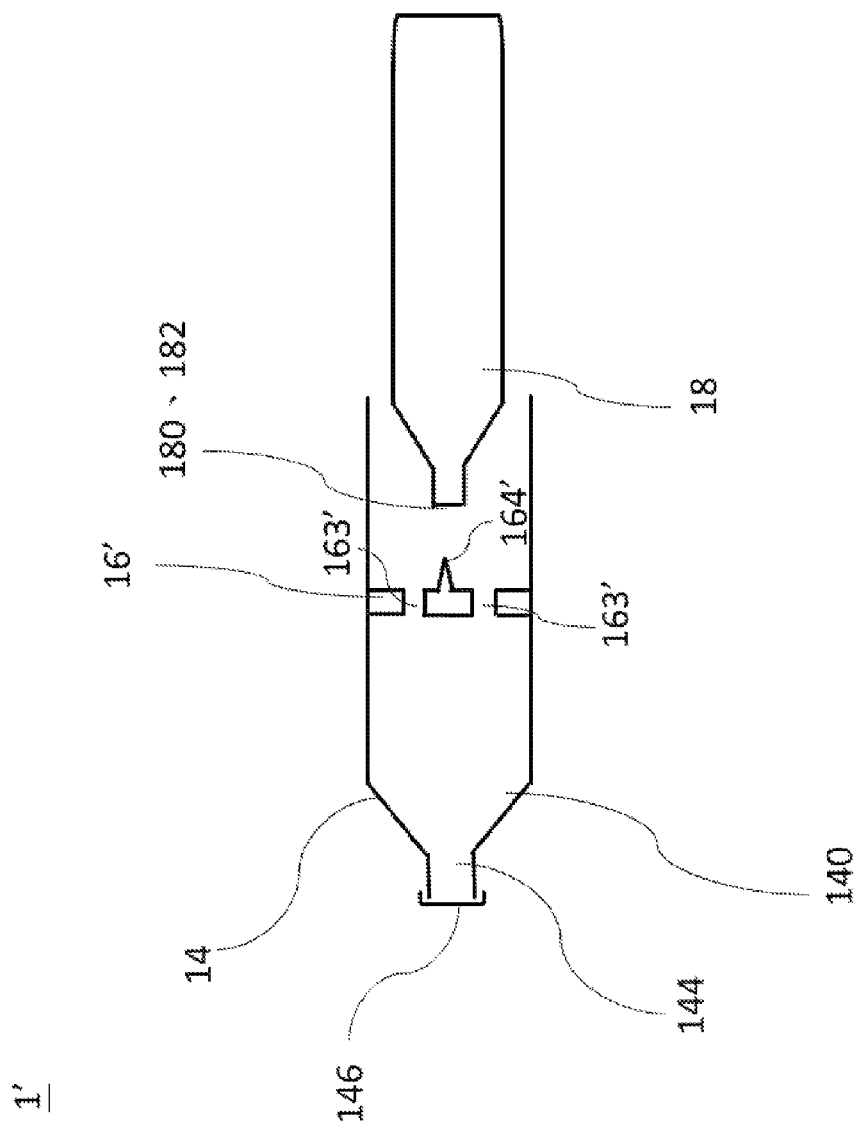
FIG. 1B is a schematic section view of a syringe of second implementation in the first embodiment in accordance with the present invention.

Please refer to FIG. 1B. FIG. 1B is a schematic section view of showing the syringe 1' of another implementation in the first embodiment of the present invention. In this implementation of the first embodiment, the most of the components is the same as that of the syringe 1 as shown in FIG. 1A, and the difference is that the sleeve piston 16' includes two through-holes 163' which is arranged around the protrusion 164' and there is no opening at the front end of the protrusion 164'. Two ends of the sleeve piston 16' is communicated with each other by the through-holes 163, when the vessel opening 180 of the pressure vessel 18 is contacted to the protrusion 164', the protrusion 164' is pierced through the vessel lid 182 to destroy the airtight status of the pressure vessel 18 such that the fluid in the pressure vessel 18 can flow into another end of the sleeve piston 16' through the through-hole 163'.

Figure 2:
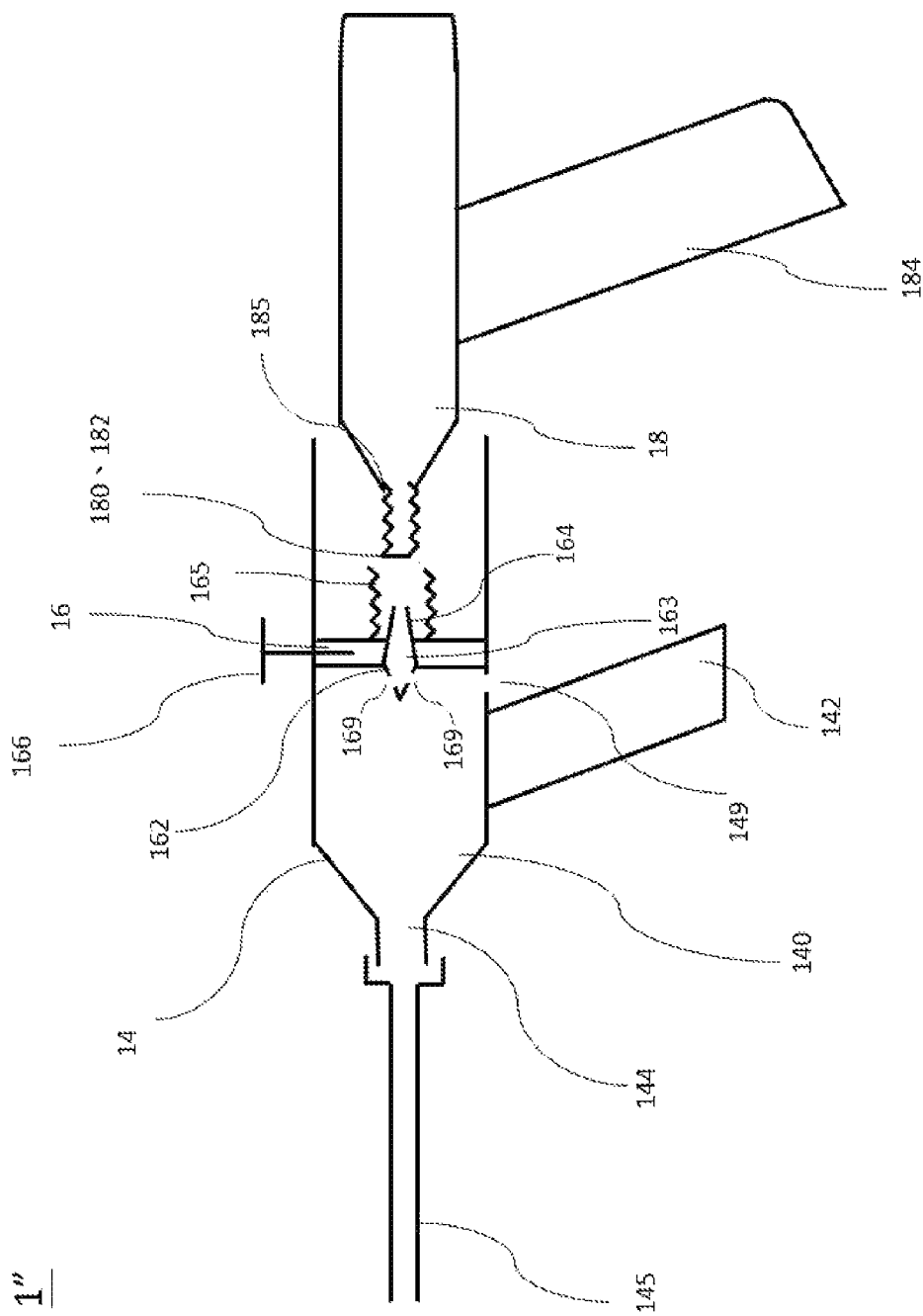
FIG. 2 is a schematic section view of a syringe the other implementation in the first embodiment in accordance with the present invention.

Next, please refer to FIG. 2. FIG. 2 is a schematic section view of showing the syringe 1" of another implementation in the first embodiment of the present invention. As shown in FIG. 2, the difference between the syringe 1" and the syringe 1 of FIG. 1A is that the sleeve piston 16 of the syringe 1" further includes a piston bolt 166. The status of the piston bolt 166 is to be adjusted to open or close. When the piston bolt 166 is closed, the sleeve piston 16 is fixed to the first sleeve 14 such that the piston bolt 166 can control the sleeve piston 16 that moves inside of the first sleeve 14. Further, the piston front opening 162 of the sleeve piston 16 can change the fluid that flows out of the flow direction of the piston front opening by another structure. For example, the piston front opening 162 can divide into one or more flow controlling ports 169. The flow controlling port 169 is not faced to the second sleeve opening 164 to avoid the fluid flowing out through the second sleeve opening 164, when the fluid in the pressure vessel 18 flowed into the first accommodating space 140. In another embodiment, at least one accommodating-space hole 149 is further disposed on the wall of the first sleeve 14, and the accommodating space is communicated with outside by the accommodating-space hole 149. When the fluid is flowed into the first accommodating space 140, the pressure inside of the first accommodating space 140 is to be equilibrated by the accommodating-space hole 149. In another embodiment, the first sleeve opening 144 may be further connected to a pipe 145 for the auxiliary injection.

To compare the syringe 1" with the syringe 1, for the syringe 1", a sleeve handle 142 can further arrange outside of the first sleeve 14 to facilitate the user grips the first sleeve 14. Meanwhile, a vessel shaft 184 corresponding to the sleeve handle 142 is further arranged on the pressure vessel 18 to increase the grip available. It should be noted that the shape, amount or the arrangement of the sleeve handle 142 and the vessel shaft 184 are not limited in the present invention. Contrast to the syringe 1, for the syringe 1", the engagement mechanism is further arranged at the junction between the sleeve piston 16 and the pressure vessel 18. For example, a female screwing structure 165 is arranged adjacent the protrusion 164 of the sleeve piston 16 and a male screwing structure 185 is arranged at the vessel opening 180 of the pressure vessel 18. Thus, the sleeve piston 16 is connected to the pressure vessel 18 by screwing the female screwing structure 165 to the male screwing structure 185, but the type of the engagement mechanism is not limited in the present invention.

Figure 3:
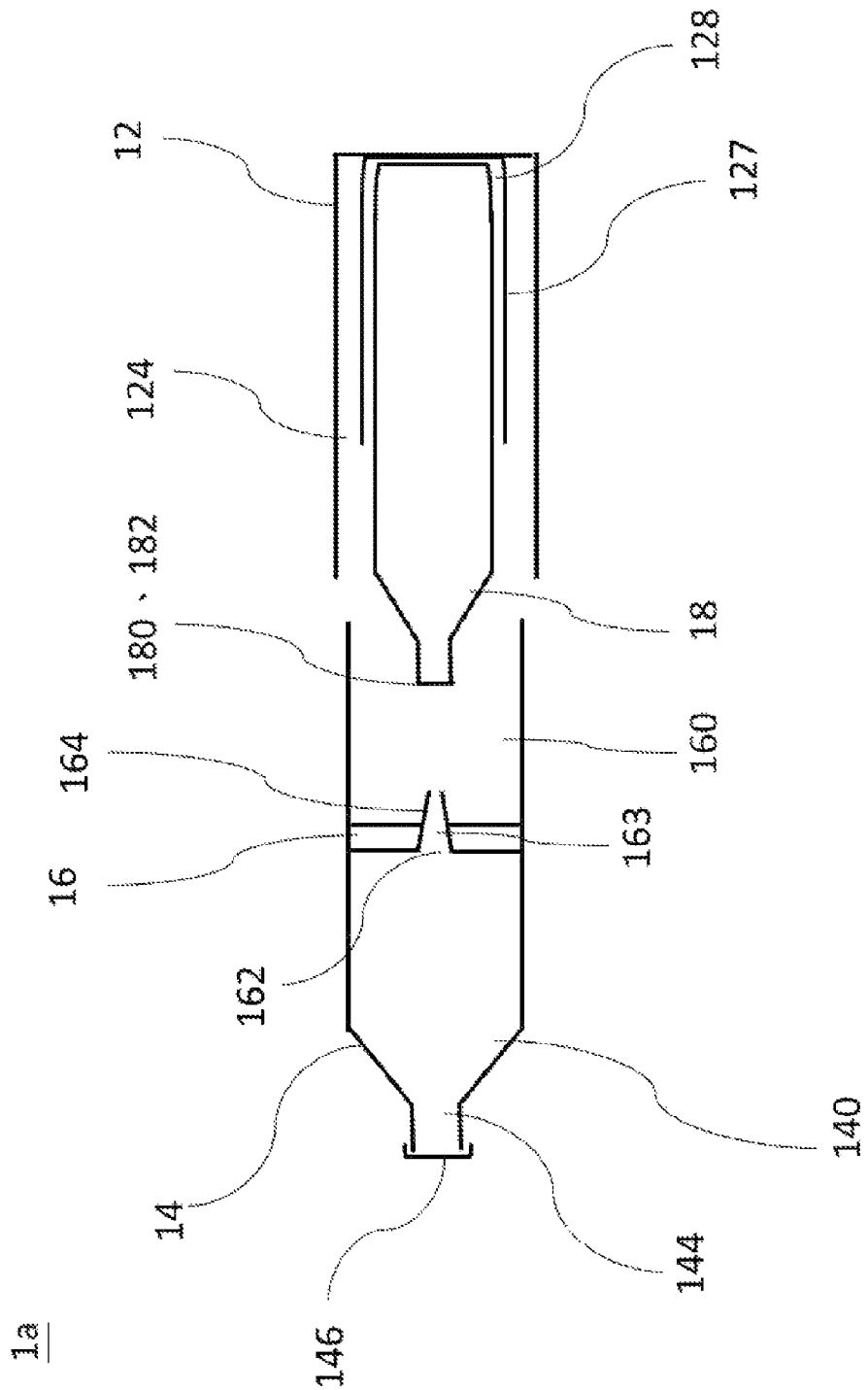
FIG. 3 is a schematic section view of the syringe of the second embodiment in accordance with the present invention.

Please refer to FIG. 3. FIG. 3 is a schematic section view of showing a syringe 1a of a second embodiment of the present invention. As shown in FIG. 3, the syringe 1a includes a first sleeve 14, a sleeve piston 16 and a pressure vessel 18 as shown in FIG. 1A. The difference between the syringe 1a and the syringe 1 is that the syringe 1a further includes a second sleeve 12. The second sleeve 12 includes a closed end and an opening end. The second sleeve 12 includes a sleeve inner tube 127 therein, and one end of the sleeve inner tube 127 is connected to the closed end of the second sleeve 12. The diameter of the sleeve inner tube 127 is smaller than that of the second sleeve 12 and the length of the sleeve inner tube 127 is smaller than that of the second sleeve 12. A space between the sleeve inner tube 127 and the second sleeve 12 is a sleeve outer tank 124 and another space in the sleeve inner tube 127 is sleeve inner tank 128, in which one end of the pressure vessel 18 can accommodate in the sleeve inner tank 128.

After the pressure vessel 18 is disposed in the sleeve inner tank 128, the engaged end of the first sleeve 14 is engaged the sleeve piston 16 and is faced to the opening end of the second sleeve 12, and the first sleeve 14 is moved toward the opening end of the second sleeve 12. When the portion of the first sleeve 14 is disposed into the second sleeve 12, the vessel opening 180 of the pressure vessel 18 is disposed into the second accommodating space 160 of the sleeve piston 16 and the piston front opening 162 of the sleeve piston 16 is faced and engaged to the vessel opening 180 so as to the protrusion 164 is pierced through the vessel lid 182 to communicate the piston front opening 162 with inside of the pressure vessel 18 and to destroy the airtight status of the pressure vessel 18. As mentioned before, because the pressure of the fluid in the pressure vessel 18 is larger than the environment pressure, when the vessel lid 182 is pierced to communicate the piston front opening 162 with inside of the pressure vessel 18, the fluid in the pressure vessel 18 is to be flowed into the first accommodating space 140 of the first sleeve 14 due to the pressure difference. For the conditions of the fluid flows into the first accommodating space 140 which is similar to the syringe 1 and thus it is not to be described in detail herein. In addition, the first sleeve 14 further includes at least one handle and the second sleeve 12 also further includes a shaft which is arranged on outside of the second sleeve 12. The functions of the handle and the shaft are similar to above sleeve handle 142 and the vessel shaft 184 respectively. Otherwise, the function for the first sleeve 14 of the syringe 1a including a accommodating-space hole, flow controlling port, tube and the piston bolt are similar to that of the accommodating-space hole 149, the flow controlling port 169, the pipe 145, and the piston bolt 166 of the syringe 1", and it is not to be described in detail herein.

Figure 4A:
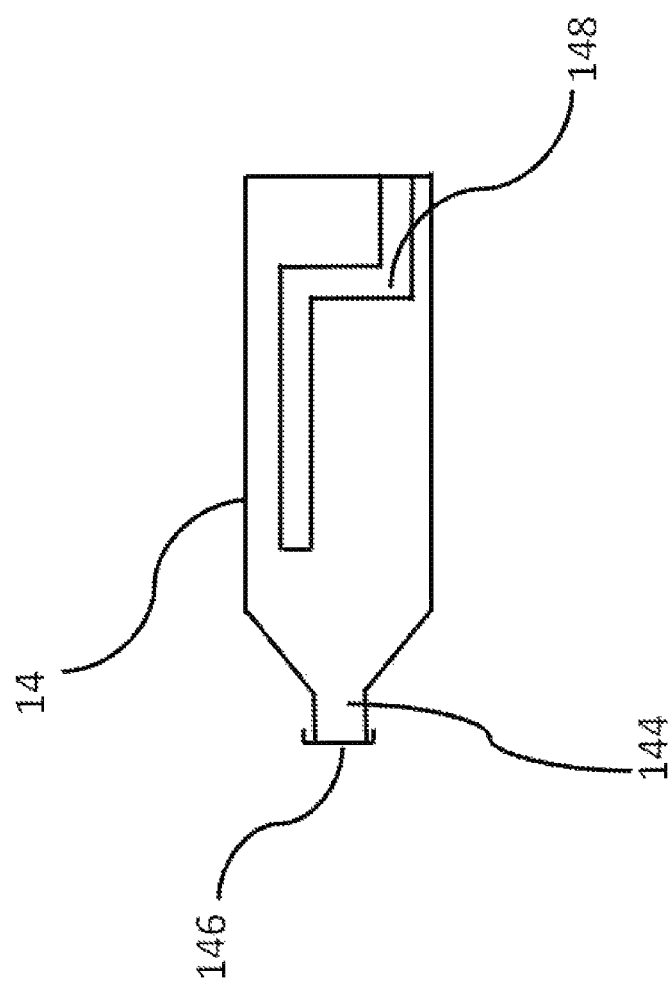
FIG. 4A is a schematic lateral view of a first sleeve in a first embodiment in accordance with the present invention.
Figure 4B:
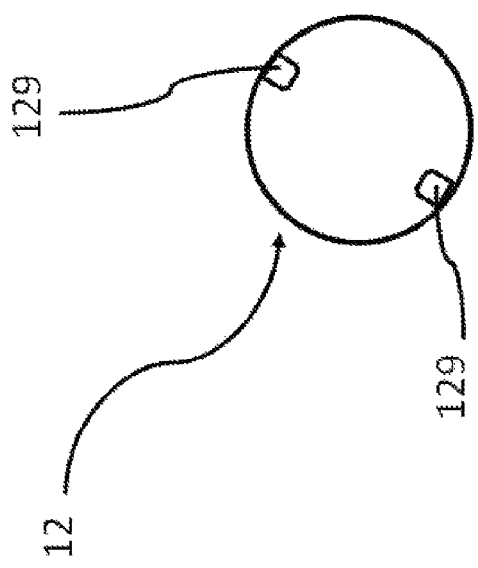
FIG. 4B is a schematic front view of a second sleeve in a second embodiment in accordance with the present invention.

In another embodiment, the junction position at each component of syringe 1a may include an engagement mechanism. For example, the vessel opening 180 of the pressure vessel 18 is screwed into sleeve piston 16 by the corresponding screw structures as the vessel opening 180 of the syringe 1" and the sleeve piston 16 in FIG. 2A. In addition, the first sleeve 14 can also be engaged with the second sleeve 12 by the corresponding screw structure. Also, as shown in FIG. 4A and FIG. 4B, the outside surface of the first sleeve 14 includes one or more trench 148 and inside of the second sleeve 12 includes one or more bumps 129 such that the trench 148 is opposite to the bumps 129 and the bumps 129 is accommodated in the trench 148. Thus, when the first sleeve 14 is engaged with the second sleeve 12, the bump 129 is to be moved along the trench 148. In an embodiment, the trench 148 in the extension direction of the outside surface of the first sleeve 14 is to be changed. For example, the trench 148 on the outside surface of the first sleeve 14 is S-shaped. Obviously, when the bump 129 is moved along the varied extension direction to let the first sleeve 14 that is engaged with the second sleeve 12 in relative rotation, such that the first sleeve 14 is engaged fixedly with the second sleeve 12, but the engagement mechanism between the first sleeve 14 and the second sleeve 12 is not limited in the present invention.

Figure 5:
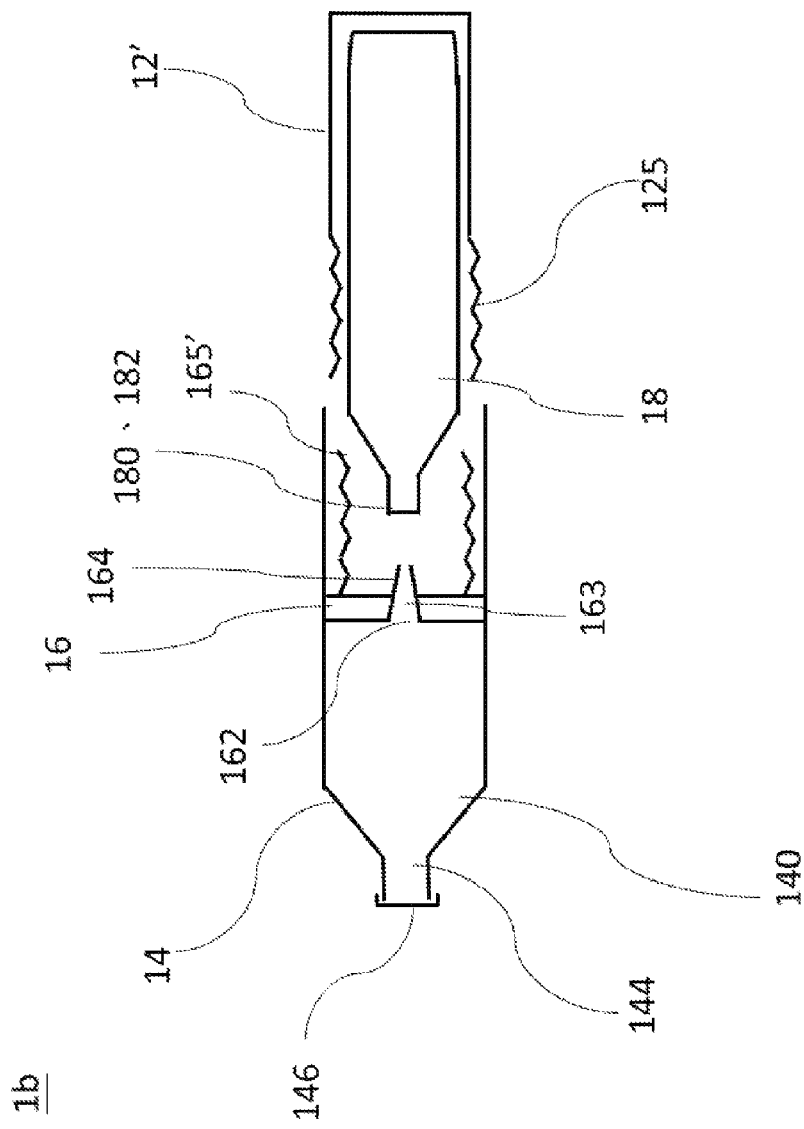
FIG. 5 is a schematic section view of a syringe in a third embodiment in accordance with the present invention.

Please refer to FIG. 5. FIG. 5 is a schematic section view of the syringe 1b of the third embodiment of the present invention. As shown in FIG. 5, the syringe 1b includes the first sleeve 14, the sleeve piston 16 and the pressure vessel 18 as in shown in FIG. 1A. The difference between the syringe 1b and the syringe 1 is that the syringe 1b further includes a second sleeve 12'. The second sleeve 12' includes a closed end and an opening end, in which the diameter of the second sleeve 12' is smaller than that of the engaged end of the first sleeve 14 and the pressure vessel 18 can accommodate into the second sleeve 12'. Obviously, the second sleeve 12' in the pressure vessel 18 can dispose in the first sleeve 14 by way of the vessel opening 180 of the pressure vessel 18 is disposed toward the engaged end of the first sleeve 14 such that the portion of the second sleeve 12 is disposed in the first sleeve 14 and the vessel opening 180 is engaged with the protrusion 164 of the sleeve piston 16. The operation condition and other components of the syringe 1b are similar to the syringe 1 and they are not to be described herein. In addition, the engagement mechanism is disposed at the junction between the first sleeve 14 and the second sleeve 12'. For example, inside of the first sleeve 14 includes a female screwing structure 165' and outside of the second sleeve 12' includes a male screwing structure 125. As a result, the first sleeve 14 is engaged with the second sleeve 12' by the female screwing structure 165' is screwed the male screwing structure 125. But the type of the engagement mechanism is not limited in the present invention. In another embodiment, the syringe 1b includes the accommodating-space hole, the flow controlling port, the piston bolt and the sleeve handle on the outside of the first sleeve 14 and the sleeve shaft on outside of the second sleeve 12' and the arrangement and the function of above components are similar to that of the syringe 1" and syringe 1a, and it is not to be described herein.

Please refer to FIG. 6. FIG. 6 is a schematic section view of showing the syringe 1c of the fourth embodiment of the present invention. As shown in FIG. 6, the syringe 1c includes the first sleeve 14 and the pressure vessel 18 as shown in FIG. 1A. The difference between the syringe 1c and the syringe 1 is that one end of the sleeve piston 16" of the syringe 1c includes a piston front opening 162", a through-hole 163" and a protrusion 164". Another end of the sleeve piston 16" is a piston back opening 167" which is opposite to the piston front opening 162". An second accommodating space 160" is disposed between two ends of the sleeve piston 16". When the sleeve piston 16" is disposed in the first sleeve 14, the second accommodating space 160" is communicated with the first accommodating space 140 of the first sleeve 14 through the through-hole 163". The second accommodating space 160" of the sleeve piston 16" can accommodate the pressure vessel 18 therein and further includes a piston cover 168 for sealing the piston back opening 167". For the pressure vessel 18 is disposed in the second accommodating space 160", the vessel opening 180 is engaged with the protrusion 164" of the sleeve piston 16". The other components of the syringe 1c and the operation are similar to the syringe 1 and it is not to be described herein. In addition, the piston cover 168" is engaged with the sleeve piston 16 through the engagement mechanism, such as the screw structure with corresponding thread structure, the corresponding bump and trench, and it is not to be described herein. In another embodiment, the arrangement and the function for the accommodating-space hole, the flow controlling port, the piston bolt, the pipe, the sleeve handle on the outside of the first sleeve 14 or the shaft on the outside of the sleeve piston 16" of the syringe 1c are similar to the syringe 1" or syringe 1a and it is not to be described herein.

For the syringe 1. 1', 1", 1a, 1b, and 1c of the present invention, when the vessel lid 182 of the pressure vessel 18 is destroyed, the airtight status of the pressure vessel 18 is destroyed to let the pressure vessel 18 be communicated with the first accommodating space 140 of the first sleeve 14. For the pressure vessel 18 is provided for accommodating the mixture which is mixed by high-pressure gas and the colloidal, the mixture in the pressure vessel 18 is entered into the first accommodating space with normal pressure and is not injected into the outside of the syringe 1, 1', 1", 1a, 1b or 1c. Meanwhile, a large amount of the bubbles is to be generated by the high-pressure gas such that the mixture is to be formed as a foam-like material and then by the movement between the first sleeve 14 and the sleeve piston 16, the foam-like material is injected out of the syringe 1, 1', 1", 1a, 1b, or 1c through the first sleeve opening 144. Thus, the convenience for the syringe for injecting the foam-like material is increased.

The present invention provides the syringes 1, 1', 1", 1a, 1b and 1c in various embodiment, the above various type of syringes 1, 1', 1", 1a, 1b and 1c such as the pistol type includes the corresponding handle and shaft and the injection type for directly driving each components, such that the syringes 1, 1', 1", 1a, 1b and 1c of the present invention can apply for any operation condition. In addition, the sleeve opening 144 of the first sleeve 14 can further engage with the pipe 145 or other similar auxiliary components but it is not limited herein.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A syringe, comprising:
   a first sleeve having an opening end and an engaging end, the opening end of the first sleeve having a sleeve opening;
   a sleeve piston having two ends with one end thereof having a protrusion, the two ends of the sleeve piston being communicated with each other via at least one through hole, the sleeve piston being disposed in the first sleeve to be movable, one of the two ends of the sleeve piston without the protrusion facing toward the opening of the first sleeve and being spaced from the opening of the first sleeve with a distance;
   a pressure vessel containing a fluid with a pressure that is larger than an environment pressure and having a vessel opening disposed to face the protrusion and sealed by a vessel lid;
   a second sleeve having a closed end and an opening end being opposite to the closed end, wherein the second sleeve has a sleeve inner tube,
   wherein the sleeve inner tube has a closed end which is connected to the closed end of the second sleeve, a length of a peripheral wall of the sleeve inner tube being shorter than a length of a peripheral wall of the second sleeve, and a gap existing between the peripheral wall of the sleeve inner tube and the peripheral wall of the second sleeve,
   wherein when the first sleeve is assembled with the second sleeve and the protrusion pierces the vessel lid, the peripheral wall of the first sleeve inserts into the gap between the peripheral wall of the sleeve inner tube and the peripheral wall of the second sleeve, the peripheral wall and the closed end of the sleeve inner tube and the sleeve piston define a space, and the pressure vessel is stabilized inside the sleeve inner tube and thereby in the space defined by the sleeve inner tube and the sleeve piston,
   wherein when the first sleeve is assembled with the second sleeve and the peripheral wall of the first sleeve inserts into the gap between the peripheral wall of the sleeve inner tube and the peripheral wall of the second sleeve, the peripheral walls of the first sleeve, the sleeve inner tube, and the second sleeve are assembled to form a triple-layer configuration, and
   wherein when the protrusion pierces the vessel lid, the fluid inside the pressure vessel flows into a first accommodating space in the first sleeve through the vessel opening and the at least one through-hole.

2. The syringe according to claim 1, wherein the engaging end of the first sleeve is disposed to face toward the opening end of the second sleeve to be partly accommodated in the second sleeve so that a portion of the first sleeve is disposed in the second sleeve.

3. The syringe according to claim 1, wherein the opening end of the second sleeve is disposed to face toward the engaging end of the first sleeve to be partly accommodated in the first sleeve so that a portion of the second sleeve is disposed in the first sleeve.

4. The syringe according to claim 1, wherein the sleeve piston further comprises a piston back opening and a second accommodating space, and the pressure vessel is disposed in the second accommodating space of the sleeve piston, and the piston back opening is sealed by a piston lid.

5. The syringe according to claim 1, wherein the first sleeve further has a sleeve handle formed on an outer edge of the first sleeve.

6. The syringe according to claim 1, wherein the sleeve opening of the first sleeve is sealed with a cover.

7. The syringe according to claim 1, wherein the sleeve opening is connected with a pipe.

8. The syringe according to claim 1, wherein pressure of the fluid in the pressure vessel ranges between 2 atm and 150 atm.

9. The syringe according to claim 1, wherein the sleeve piston further has a piston bolt to fix the sleeve piston on the first sleeve.

10. The syringe according to claim 1, wherein the sleeve piston further comprises a piston opening being divided into a plurality of flow controlling ports that are not facing toward the first sleeve opening.

11. The syringe according to claim 1, wherein a wall surface of the first sleeve has at least one through hole communicating the inside of the first sleeve with the outside of the first sleeve.

12. The syringe according to claim 1, wherein the at least one through hole is positioned around the protrusion.

13. The syringe according to claim 1, wherein an outside surface of the first sleeve 14 includes a trench and an inside surface of the second sleeve includes a bump; wherein the trench and the bump are corresponding to each other, whereby when the first sleeve is assembled with the second sleeve, the first sleeve is fixedly engaged fixed with the second sleeve.

14. The syringe according to claim 1, wherein the first sleeve includes a first screwing structure and the second sleeve includes a second screwing structure corresponding to the first screwing structure; wherein the screwing structure is screwed with the second screwing structure, whereby when the first sleeve is assembled with the second sleeve, the first sleeve is fixedly engaged with the second sleeve.

* * * * *